US006396576B1

(12) United States Patent
Bleyle

(10) Patent No.: US 6,396,576 B1
(45) Date of Patent: May 28, 2002

(54) METHOD FOR DETERMINING SHADOWLINE LOCATION ON A PHOTOSENSITIVE ARRAY AND CRITICAL ANGLE REFRACTOMETER EMPLOYING THE METHOD

(75) Inventor: Kyle R. Bleyle, Lancaster, NY (US)

(73) Assignee: Leica Microsystems Inc., Depew, NY (US)

( * ) Notice: Subject to any disclaimer, the term of this patent is extended or adjusted under 35 U.S.C. 154(b) by 0 days.

(21) Appl. No.: 09/794,991

(22) Filed: Feb. 27, 2001

(51) Int. Cl.[7] ............................................... G01N 21/41
(52) U.S. Cl. ....................................... 356/128; 356/134
(58) Field of Search ................................. 356/128, 129, 356/130, 131, 132, 133, 134, 135, 136, 137

(56) References Cited

U.S. PATENT DOCUMENTS

| | | | |
|---|---|---|---|
| 4,640,616 A | 2/1987 | Michalik | ..................... 356/136 |
| 5,617,201 A | 4/1997 | Kahre | ......................... 356/135 |
| 6,172,746 B1 | 1/2001 | Byrne et al. | ................. 356/135 |

Primary Examiner—Frank G. Font
Assistant Examiner—Tu T. Nguyen
(74) Attorney, Agent, or Firm—Simpson, Simpson & Snyder, PLLC

(57) ABSTRACT

A method for determining a cell crossing number of a shadowline between illuminated and dark regions of a linear scanned array of photosensitive cells, and an automatic refractometer using the method, are disclosed. The array is scanned to extract a response signal from each of the photosensitive cells, and the response signals are converted from are converted from analog form to digital pixels, thus yielding a set of data points that collectively represent an illumination distribution curve over the array. A range of cells within which the shadowline resides is established by analyzing the illumination curve data. The second derivative of the illumination distribution curve over the established range of cells is calculated and the greatest positive area bounded by the second derivative is identified. The centroid of the greatest positive area is found and its cell number coordinate is deemed the cell crossing number of the shadowline. The method provides improved precision to better accommodate varying levels of illumination intensity.

10 Claims, 7 Drawing Sheets

METHOD FOR DETERMINING SHADOWLINE LOCATION ON A PHOTOSENSITIVE ARRAY AND CRITICAL ANGLE REFRACTOMETER EMPLOYING THE METHOD

BACKGROUND OF THE INVENTION

The present invention relates generally to methods for determining the location of a transitional boundary or "shadowline" between an illuminated region and a dark region on a linear scanned array of photosensitive cells, such methods being particularly applicable to critical angle refractometers wherein shadowline location is correlated to index of refraction of a test sample.

Refractometers are widely used for measuring the refractive index of a sample. In refractometers designed to measure solid and/or liquid samples, the critical angle of total reflection is measured by directing an obliquely incident convergent beam of light at a surface-to-surface boundary between a high refractive index prism and the sample and then observing a portion of the light after interaction at the boundary. In transmitted light refractometers, light that is transmitted through the sample and prism is observed, while in reflected light refractometers, the light that is reflected due to total reflection at the surface-to-surface boundary is observed. In either case, an illuminated region is produced over a portion of a detection field of view, and the location of the shadowline between the illuminated region and an adjacent dark region in the detection field of view allows the sample refractive index to be deduced geometrically. In simpler hand-held refractometers used in industry, a reticle scale is superimposed in the field of view and the user looks through an eyepiece to observe the location of the shadowline with respect to the reticle scale, which is marked so as to provide desired information such as percentage concentration of solids in the sample.

Automatic refractometers were developed to remove the guesswork associated with visually determining shadowline location with respect to a reticle scale, thus improving the accuracy (closeness to the true value) and precision (repeatability regardless of accuracy) of measurement readings. U.S. Pat. No. 4,640,616 issued Feb. 3, 1987 to Michalik discloses an automatic Abbe refractometer wherein a linear scanned array (LSA) of photosensitive elements or "cells" is arranged to detect light totally reflected at a sample/prism boundary. In a commercial embodiment, the linear scanned array includes a straight line of charge-coupled device (CCD) cells that are scanned electronically to provide a series of pulse signals each having an amplitude proportional to the amount of illumination received by the cell from incident light. Light received by the linear scanned array divides the array into an illuminated region and an adjacent dark region, thereby forming a shadowline on the array. The particular cell or interpolated inter-cell fraction at which the shadowline falls on the linear scanned array, known as the "cell crossing number," is determined by the index of refraction of the sample substance placed in contact with the optical means. Thus, a method is required for evaluating the pulse signals from the photosensitive cells to find the cell crossing number. The cell crossing number may then be used to provide a measurement value of the index of refraction or a percent concentration of dissolved solids, such as sucrose, in the sample medium.

The Michalik patent teaches a "thresholding" approach for processing the light intensity signals from the array cells to determine the cell crossing number. This approach is represented graphically at FIG. 3 herein. Under a thresholding approach, an empty baseline or reference scan is taken without a sample (that is, with respect to air) and stored to establish a reference illumination curve. The curve from the reference scan is then scaled by a predetermined fixed scale factor, for example 94%, to provide a threshold curve as indicated in FIG. 4. The resulting cell where the sample scan curve intersects the threshold curve is declared the cell crossing number.

This approach yields precise and accurate measurements, however the incident light levels must be controlled to a high degree, as it is crucial that the reference and sample scans are comparable. Any deviation in intensity levels will cause erroneous readings. Since the disclosed automatic refractometer is a "reflected light" refractometer, light reaching the linear scanned array never passes through the sample, it is possible to adequately control incident light levels by controlling source luminance. An advantage of the thresholding approach is that a fresh reference scan is taken every time the instrument is turned on, so gradual changes in the response characteristics of each photosensitive cell over the lifetime of the cell (known as "response drift") do not affect instrument performance. Moreover, use of a reference scan compensates for cell-to-cell variance in response to a given level of illumination.

The use of a reference scan and scaled threshold is problematic in "transmitted light" refractometers because, unlike the reflected light refractometer discussed above, light must pass through the sample before reaching the detector array. Consequently, sample-dependent factors such as the color, opaqueness, thickness, and homogeneity of the sample make it impractical to control incident light levels at the detector array. For example, a reference scan of air may be suitable for a clear water sample, but would not be suitable for measurement of a sample with low transmissivity, such as ketchup. Another drawback of the threshold approach is that a single defective cell providing an erroneous response signal may, at the worst, distort the measurement result.

U.S. Pat. No. 5,617,201 issued Apr. 1, 1997 to Kåhre describes a reflected light refractometer using another method for determining the cell crossing number of the shadowline boundary. The method involves describing the illumination distribution curve by means of a mathematical model, and using the mathematical model to find the cell crossing number. In the described embodiment, the illumination distribution curve is represented by three different straight lines A, B, and C representing a light region of the array, a transition region of the array from light to dark, and a dark region of the array, respectively. The intersection of line B with line C is chosen as the cell crossing number. Non-linear models are also suggested. A similar approach with respect to a transmitted light refractometer is taught in U.S. Pat. No. 6,172,746 issued Jan. 9, 2001 to Byrne et al. (this patent shares a common assignee with the present application), and is illustrated herein at FIG. 5. However, the method involving intersecting "best fit" straight lines representing the transitional and dark regions of the detector array proved to be too imprecise for transmitted light applications wherein detected light levels are difficult to control. The precision attained was inadequate over the range of light intensities that this instrument can experience, and thus the method was ultimately not adopted.

BRIEF SUMMARY OF THE INVENTION

Therefore, it is a primary object of the present invention to provide a new method for determining the cell crossing number of a shadowline on a photosensitive array that is relatively immune to light intensity level variations while maintaining adequate precision.

This object is achieved by a method that is now briefly described in a preferred form. Initially, the photosensitive array is scanned to extract a response signal from each of the photosensitive cells in the array that represents the amount of illumination of the corresponding cell by incident light. The response signals from the photosensitive cells are converted from analog form to digital pixels, thus yielding a set of data points that collectively represent an illumination distribution curve over the array. A range of cells within which the shadowline resides is established by analyzing the illumination curve data. A preferred procedure for establishing a "start" cell for this range is to find the brightest cell by looking for a peak pixel value, and then step forward one cell at a time until a cell having a pixel value that is 25% of the peak pixel value is reached. A preferred procedure for establishing an "end" cell is to begin at the "start" cell and step forward one cell at a time, continually updating the lowest pixel value that is read, until a cell that has a pixel value of 105% of the lowest pixel value is found or the last cell of the array is reached. The second derivative of the illumination distribution curve over the established range of cells is calculated and the greatest positive area bounded by the second derivative is identified. Finally, the centroid of the greatest positive area is found and its cell number coordinate is deemed the cell crossing number of the shadowline.

The above method is employed in an automatic refractometer for measuring refractive index of a sample substance. The refractometer comprises a linear scanned array having a plurality of photosensitive cells and optical means for directing light onto the array, wherein the particular photosensitive cells illuminated by the light and a cell crossing number of a shadowline defined by illuminated and dark regions of the array are determined by the index of refraction of a substance placed in operative association with the optical means. The refractometer further comprises analog to digital conversion means and digital processing circuit means for carrying out the aforementioned method, and an output device for reporting a measurement result derived from the cell crossing number.

BRIEF DESCRIPTION OF THE SEVERAL VIEWS OF THE DRAWINGS

The nature and mode of operation of the present invention will now be more fully described in the following detailed description of the invention taken with the accompanying drawing figures, in which.

DETAILED DESCRIPTION OF THE INVENTION

Figure 1A:
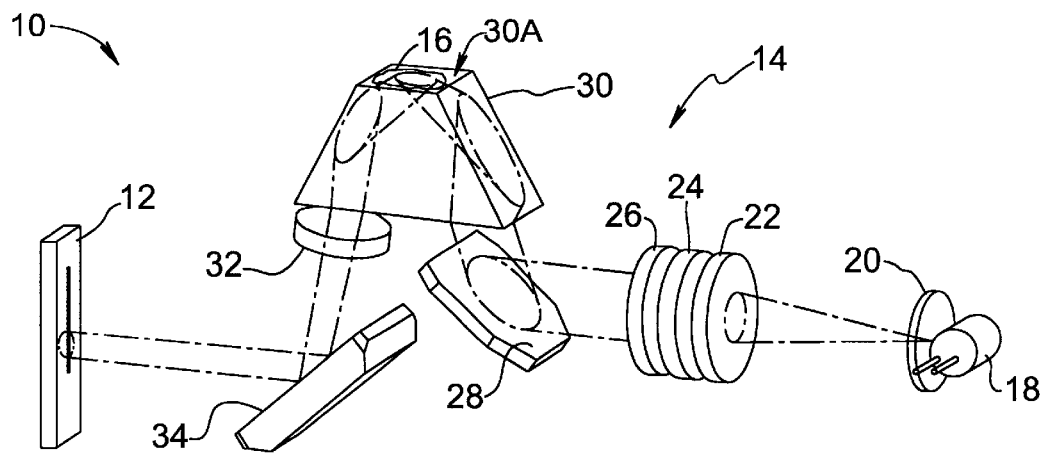
FIG. 1A is an optical schematic diagram of a reflected light refractometer formed in accordance with the present invention.
Figure 1B:
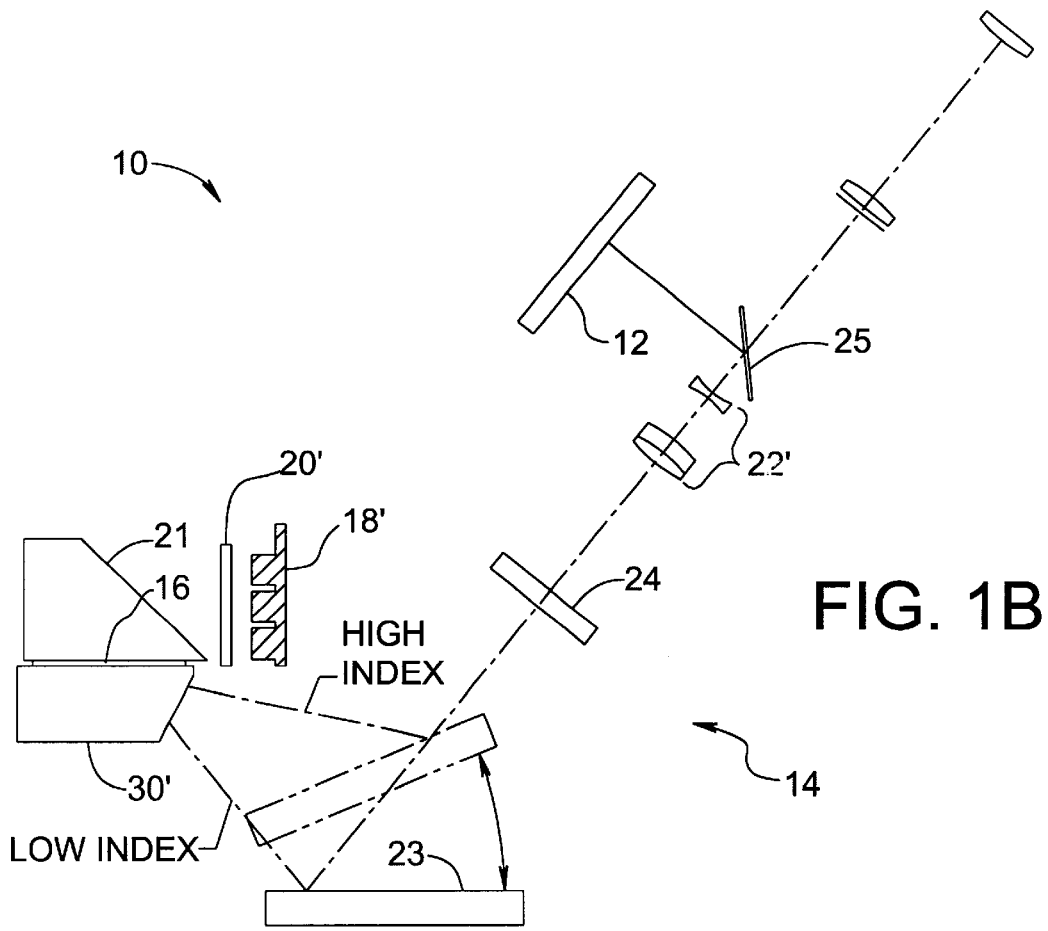
FIG. 1B is an optical schematic diagram of a transmitted light refractometer formed in accordance with the present invention

Referring initially to FIG. 1A of the drawings, a refractometer formed in accordance with the present invention is depicted schematically and identified generally by the reference numeral 10. Refractometer 10 is shown in FIG. 1A as being a reflected light refractometer similar to that taught by the aforementioned U.S. Pat. No. 4,640,616, however refractometer 10 could also be a transmitted light refractometer as shown in FIG. 1B similar to that taught by the aforementioned U.S. Pat. No. 6,172,746. Regardless of whether refractometer 10 is of a reflected light or transmitted light design, it includes a linear scanned array 12 for detecting light that is directed thereto by optical means generally identified as 14. More particularly, and as further illustrated by FIG. 2, linear scanned array 12 includes a plurality of photosensitive cells 13 that each provide a response signal during a scan, with the amplitude of each response signal being determined by the amount of illumination of the corresponding cell by incident light. Linear scanned arrays are well known in the art, and are available from a large number of manufacturers, including for example SONY.

Figure 2:
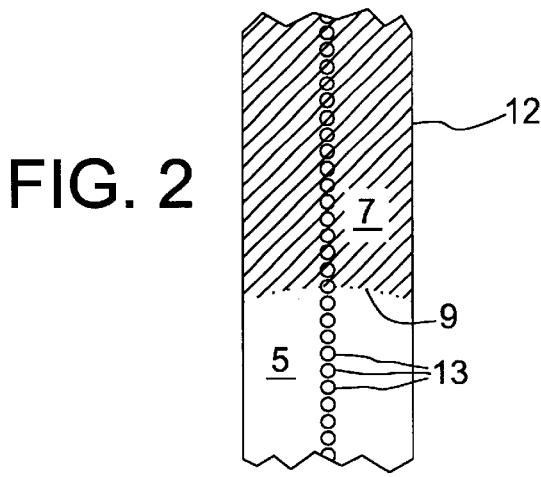
FIG. 2 is an enlarged view of the linear scanned array of photosensitive cells appearing in either FIG. 1A or FIG. 1B.

Optical means 14 functions to direct light to linear scanned array 12, with the particular cells that are illuminated by the light being determined by the index of refraction of a sample substance 16 placed in operative association with optical means 14. The optical means 14 shown in the exemplary reflected light embodiment of FIG. 1A sequentially comprises a light source 18, a diffuser 20 after the light source, a collimating lens 22 following the diffuser, a monochromatic filter 24 closely adjacent to the collimating lens for transmitting a narrow bandwidth of light with a central wavelength of 589 nm, a focusing lens 26 closely adjacent to the filter, a mirror 28 for redirecting the light into a high refractive index prism 30 having a sample surface 30A for receiving a sample substance to be tested, a compensating lens 32 serving to compensate for optical variations in prism 30, and another mirror 34 for redirecting the light in the direction of linear scanned array 12. As will be appreciated, optical means 14 provides an optical path leading to linear scanned array 12, wherein a portion of the light is transmitted out of the path through sample substance 16 and another portion of the light is internally reflected at the boundary of sample surface 30A and sample substance 16 to remain on the optical path. Accordingly, the particular cells 13 illuminated by the light will depend upon the index of refraction of sample substance 16. In FIG. 2, it can be observed that the distribution of light at linear scanned array 12 includes an illuminated region 5 and an adjacent dark region 7 defining a boundary or shadowline 9 at the transition from illuminated region 5 to dark region 7. Thus, the cell crossing number of shadowline 9 depends upon the index of refraction of sample substance 16.

The illustrated optical means is similar in large part to that described in U.S. Pat. No. 4,640,616, which is hereby incorporated by reference in the present application. Of course, it will be recognized that various optical configurations can perform a similar function, including transmitted light configurations such as that shown in FIG. 1B wherein the portion of light transmitted through the sample substance is directed to the linear scanned array and the portion of light reflected at the prism-sample boundary is directed out of the optical path. Optical means 14 of FIG. 1B sequentially comprises a light source 18', an illumination window 20' after the light source, an illumination prism 21 for illuminating the sample substance 16, a sample prism 30' supporting the sample substance, an angularly positionable mirror 23, a 589 nm monochromatic filter 24, a collimating lens system 22', and a beam splitter 25. The illustrated example of a transmitted light configuration for the optical means 14 is taught in U.S. Pat. No. 6,172,746, which is hereby incorporated by reference in the present application. The particular make up of the optical means of refractometer 10 may be left to the skilled artisan, as it is the processing of the response signals from linear scanned array 12 that is critical to the present invention. In fact, the invention in a broad sense is not limited to a refractometer, but to any application in which the location (cell crossing number) of a shadowline with respect to a detector array is sought to be determined.

Linear scanned array 12 and the various elements of optical means 14 are preferably mounted in fixed relation to each other in a housing, not shown.

Figure 3:
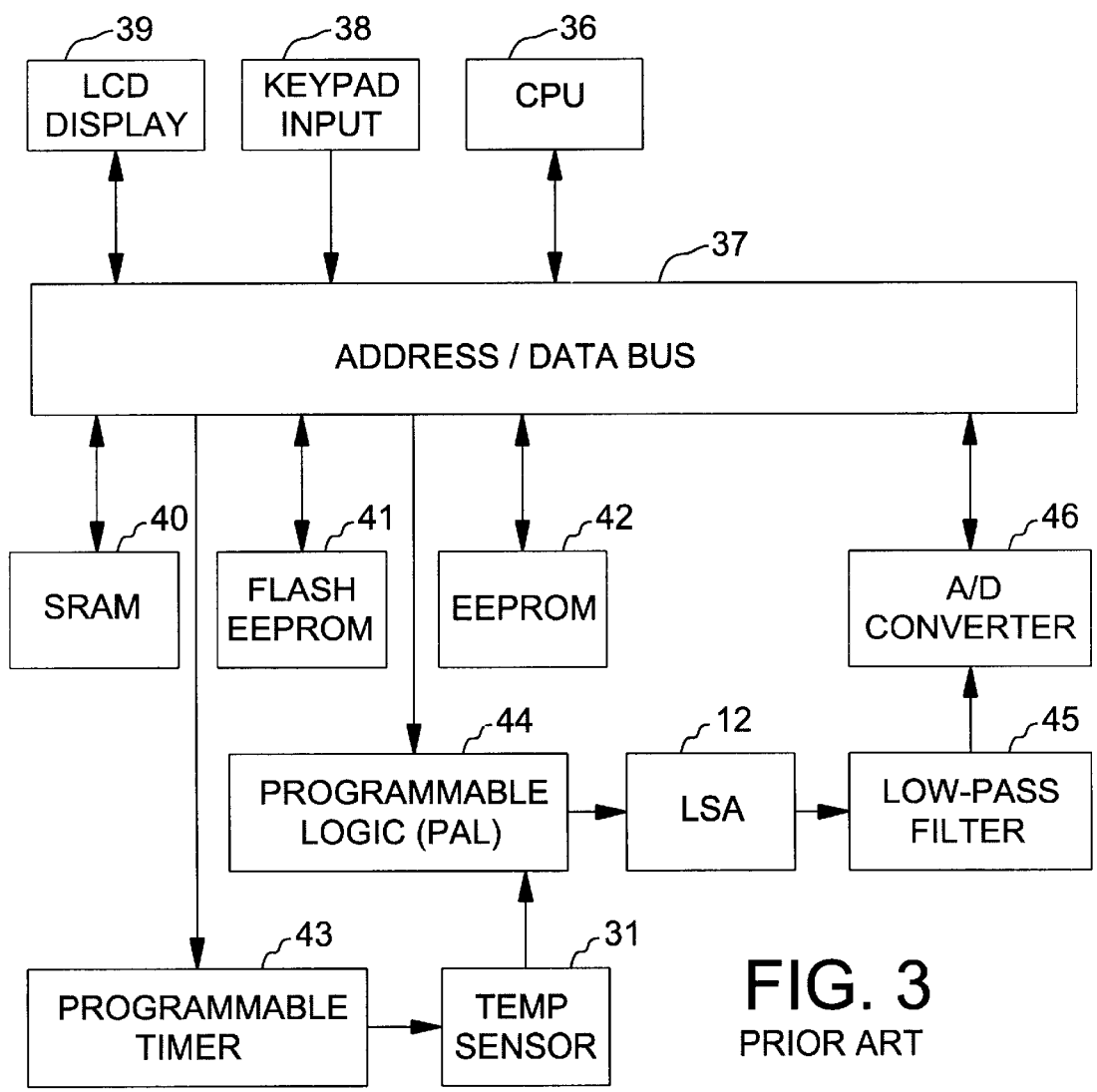
FIG. 3 is a block diagram of the signal processing circuitry associated with the linear scanned array.
Figure 4:
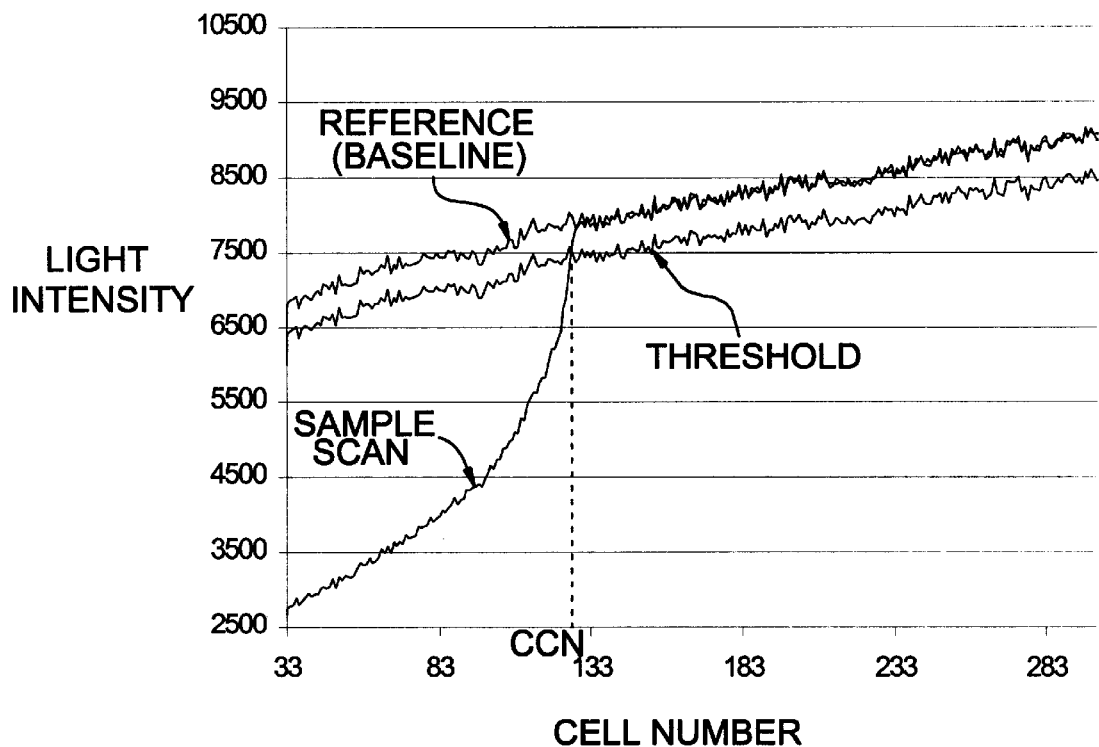
FIG. 4 is a graph showing a reference illumination curve and threshold curve with respect to a linear scanned array to illustrate a prior art method for determining the cell crossing number of a shadowline on a linear scanned array.
Figure 5:
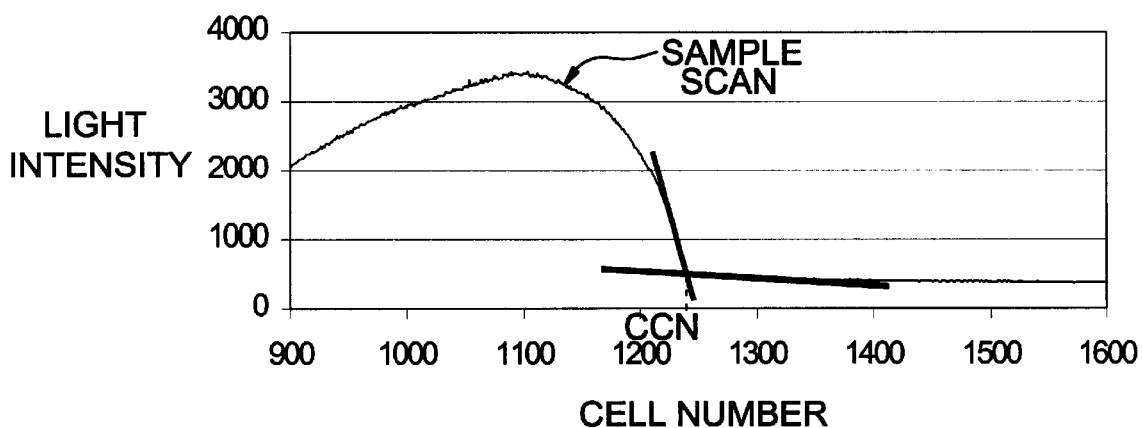
FIG. 5 is a graph showing a sample illumination curve and lines fit to the transitional and dark portions of the illumination curve to illustrate another prior art method for determining the cell crossing number of a shadowline on a linear scanned array.
Figure 6:
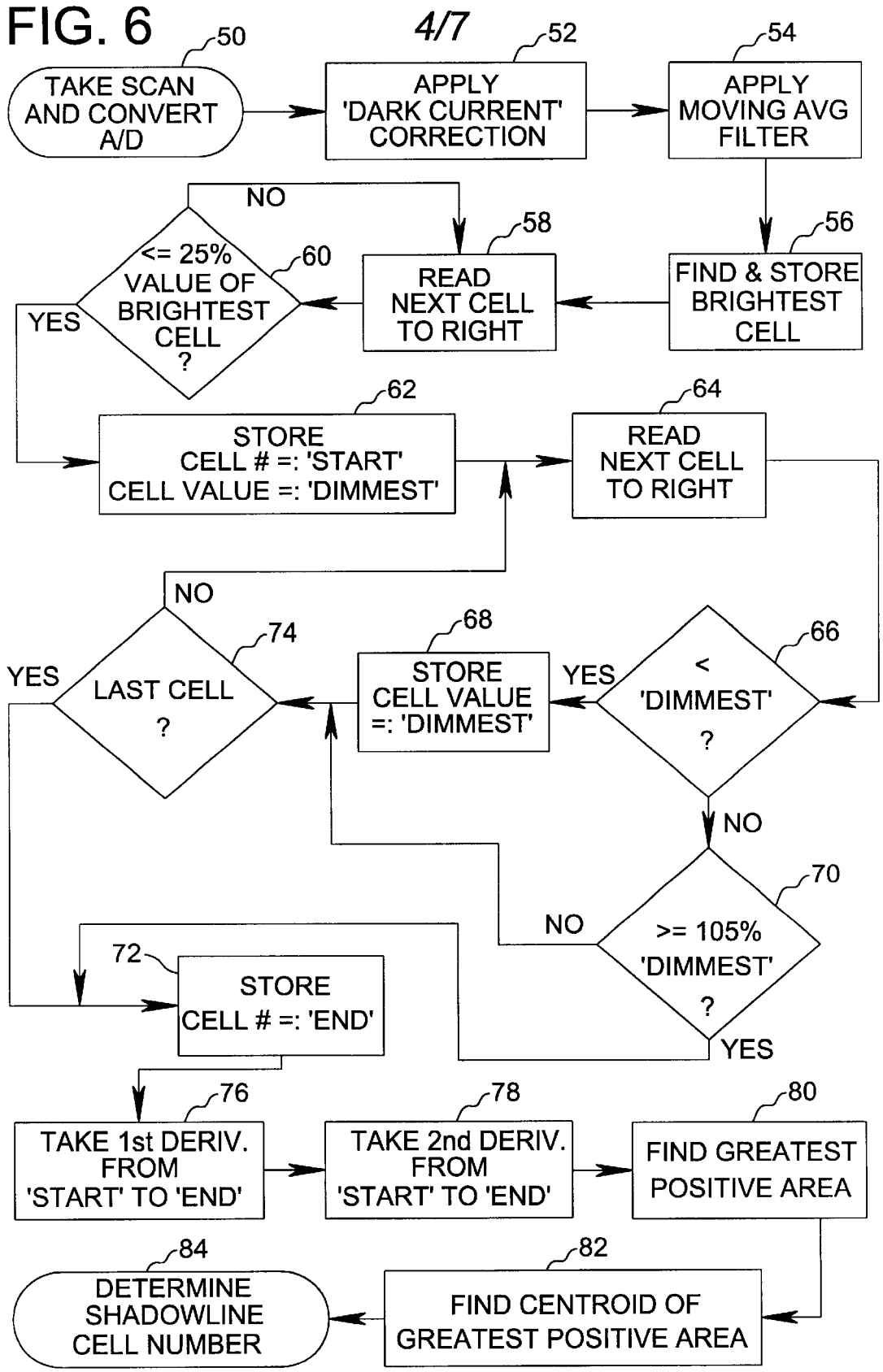
FIG. 6 is a flow chart showing the method of the present invention for determining the cell crossing number of a shadowline on a linear scanned array.

Attention is now directed to FIG. 3 of the drawings, which shows a block diagram of the electronic circuitry for processing the response signals from cells 13 of linear scanned array 12. A central processing unit 36 is linked via an address/data bus 37 to other circuitry and electronic input and output devices of refractometer 10. A keypad input 38 and an LCD display 39 are preferably provided as input and output devices, however other input devices such as a keyboard and mouse and other output devices such as a CRT monitor and printer are possible. Memory blocks include a static random access memory (SRAM) 40 for storing program variables that do not need to be saved when the instrument is switched off, a flash electrically erasable programmable read-only memory (EEPROM) 41 for storing executable code and sucrose conversion factors provided by the International Commission for Uniform Methods of Sugar Analysis; and a EEPROM 42 for storing changeable user settings, calibration data, and customizable conversion tables. The task of reading measurement information, including information from a temperature sensor 31 associated with sample prism 30, 30' and signal information from linear scanned array 12, is controlled by a programmable timer circuit 43 and a programmable logic circuit 44. The amplitude of each response signal is determined by the amount of illumination of the corresponding cell 13 by incident light since the cell was last discharged. The response signals are subjected to a low-pass filter 45 and the amplitudes of the response signals are converted from analog to digital form by an analog-to-digital converter 46, thereby providing a series of data points consisting of a cell number identifying the ordinal position of the particular cell 13 in the linear scanned array 12 and the corresponding digitized amplitude indicating the amount of illumination detected by that cell. These data collectively represent an illumination distribution curve with respect to linear scanned array 12.

Turning now to FIGS. 6–11, a preferred method according to the present invention for determining the cell crossing number of shadowline 9 based on the digitized amplitude information from the cells 13 of linear scanned array 12 will now be described. First, according to step 50, linear scanned array 12 is electronically scanned and the response pulses are digitized, as described above. The digitized response signals are referred to hereinafter as "pixels".

A dark current correction routine is run on the resulting data set under step 52. One of the two main unwanted side effects of CCD array technology is the addition of so-called "dark current" to the pixels. Dark current, which is linearly related to exposure time, is signal information created by a cell in the absence of light, and is caused by random thermal effects and other sources. Dark current correction is common in signal processing applications, but will be briefly described here. When refractometer 10 is first turned on, linear scanned array 12 is characterized for dark current noise by taking one scan at the fastest exposure possible and one scan at the slowest exposure possible, and both scans are stored in memory. The correction is applied by taking a linear interpolation of the fast and slow scans and finding the theoretical dark current that the current scan should have. In other words, if the fast-exposure dark current for a given cell is 10, and the slow-exposure dark current for that cell is 20, then an exposure speed exactly halfway between fast and slow will result in a dark current value of 15. The respective dark current value is subtracted from the current scan value of each pixel.

Dark current correction is followed by application of a moving average filter to the pixel data under step 54. The second unwanted CCD array side effect is the variation of sensitivity from cell to cell in the array. To cope with this variation, a moving average filter is applied to the data in a manner common in signal processing. The moving average filter will remove high-frequency signal components while allowing the low-frequency components to pass through. Each pixel becomes the average of the pixels generated by the cells around it. For example, in a five-point moving-average filter, pixel X is given the value (Pixel (X−2)+Pixel (X−1)+Pixel X+Pixel (X+1)+Pixel (X+2))/5).

Figure 10:
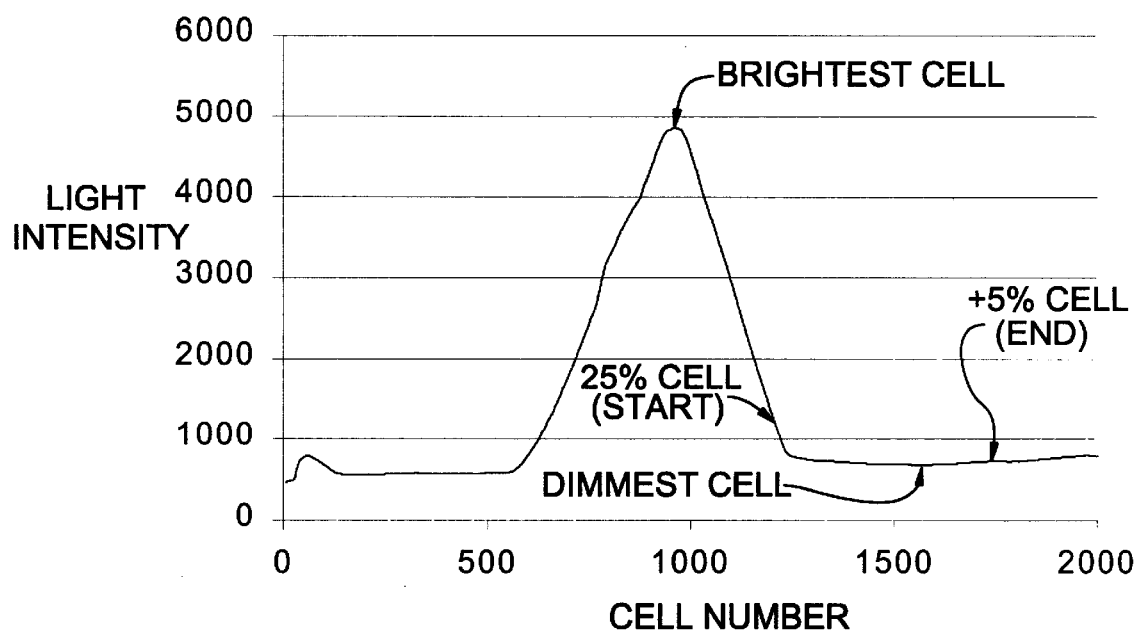
FIG. 10 is a graph showing a sample illumination curve and illustrating a preferred range-finding step used in the method of the present invention.

The next group of steps 56 through 74 involve a preferred routine for establishing a range of cells of the linear scanned array within which shadowline 9 resides, for further processing within the range. Reference is also made to FIG. 10, which offers a graphical illustration of the preferred routine. Pursuant to step 56, the entire set of pixel data is searched to find the brightest cell having the highest pixel value, and its cell number and pixel value are stored in memory. Next, in step 58, pixel data from the next cell to the right as seen in FIG. 10 is read and compared in step 60 to determine if it is less than or equal to 25% of the pixel value of the brightest cell located and stored in step 56. Step 58 is repeated until a cell meeting the 25% criterion of step 60 is reached, at which point the corresponding cell number is stored in memory as the START cell of the range, and the pixel value is stored as a DIMMEST pixel value under step 62. This procedure for assigning the START cell of the range will always provide a START cell that is well before the shadowline location and well after the brightest cell, and also helps to ensure that any anomalies in the scan are ignored. Once the START cell has been identified, the routine continues in step 64 by reading the next cell to the right as seen in FIG. 10. The pixel value is compared, in accordance with step 66, with the DIMMEST pixel value previously stored. If the compared pixel value is less than the DIMMEST pixel value previously stored, the compared pixel value is stored as the new DIMMEST pixel value in step 68. However, if the compared pixel value is not less than the DIMMEST pixel value previously stored, then the illumination curve is no longer dropping and the pixel value of the cell is checked in step 70 to determine whether it meets a predetermined end criterion. In the preferred routine, if the pixel value is greater than or equal to 105% of the DIMMEST pixel value, then the cell number is stored as the END cell at step 72. If no cell meets the 105% end criterion, a default end criterion is imposed according to step 74 such that the last cell in the array is assigned to be the END cell. If the neither the 105% criterion nor the last cell criterion is met, flow reverts back from step 74 to step 64 to read the next cell. The goal in the preferred technique for finding the END of the range, as can be seen in FIG. 10, is to find a 5% rise in the illumination curve, and failing that, to choose the last cell as the END cell. Certain types of samples can cause anomalies in the scan that are thus ignored by this step.

It is noted here that one of the benefits of the range-finding routine described in the previous paragraph is that it quickly narrows the search for the shadowline 9 and thus avoids the need for spending further computational time with respect to pixels not in the local region of the shadowline. However, as will be apparent from the description below, it is possible one could simply treat the range as including the entire line of cells 13 in linear scanned array 12, such that the first cell is START and the last cell is END, but this approach is not preferred because it fails to eliminate potential anomalies in the illumination curve that may effect results. Of course, other range-finding techniques can be employed. Consequently, the step of establishing a range of cells of the linear scanned array within which the shadowline resides is not limited to the preferred technique described above, and is intended to broadly include a simple technique establishing a range over the entire array as well as more selective techniques which narrow the range of cells relative to the entire array.

Figure 7:
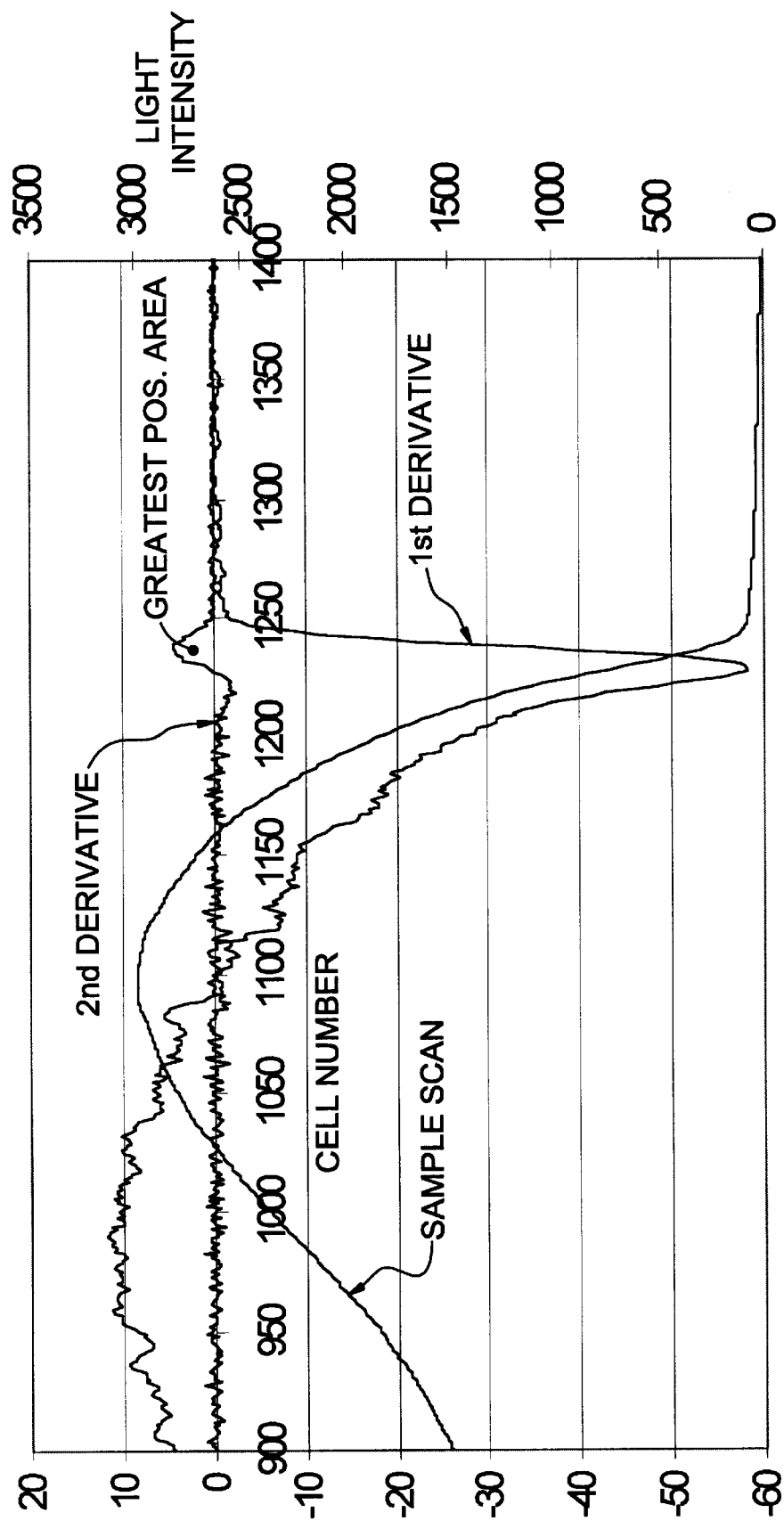
FIG. 7 is a graph showing a sample illumination curve with first and second derivatives of the sample illumination curve being plotted therewith.
Figure 8:
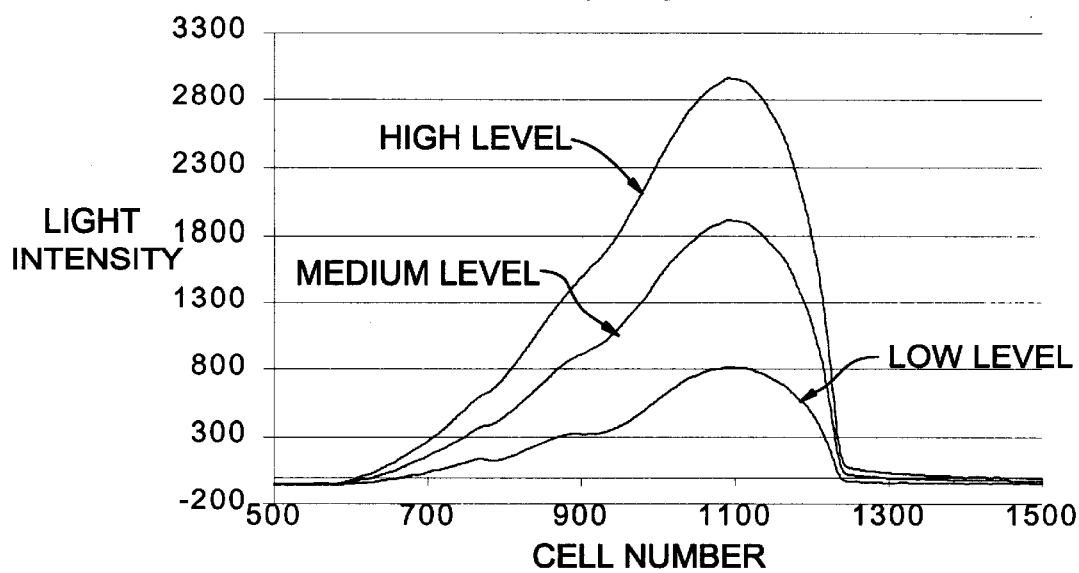
FIG. 8 is a graph showing a set of illumination curves for the same sample but with three different intensity levels of light incident upon the linear scanned array.
Figure 9:
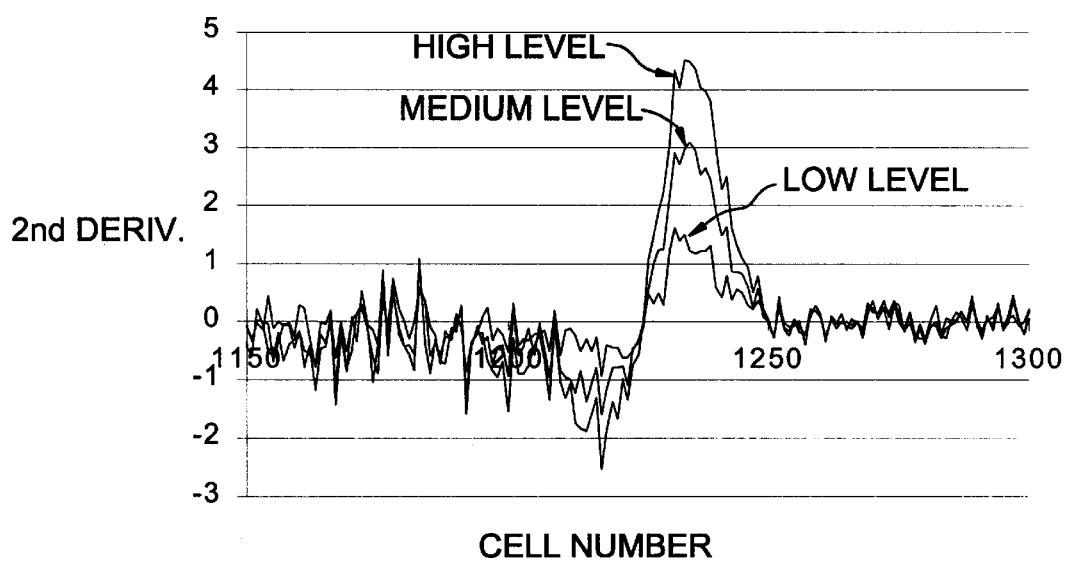
FIG. 9 is a graph showing the second derivatives of the three illumination curves shown in FIG. 8.

Returning to FIG. 6, and making reference also now to FIGS. 7 through 9, the method of the present invention for determining the cell crossing number continues by concentrating on the range of cells from START to END. More specifically, the first derivative of the illumination curve from START to END is calculated in step 76 so that the second derivative of the illumination curve from START to END can be calculated in step 78. FIG. 7 includes plots of the first and second derivatives superimposed on an illumination curve from a sample scan. The first derivative is a measure of the slope of the illumination curve, and for this application it can be computed as the difference in pixel value between adjacent cells. The second derivative is a measure of the slope of the slope of the illumination curve (that is, it is the rate-of-change of the rate-of-change). In this application, it is the difference between first derivatives of pixel values.

As can be seen in FIGS. 7 and 9, the second derivative plot provides a positive "hump" with greatest area in the vicinity of the shadowline. Importantly, as demonstrated by FIG. 9, this greatest positive area appears at the same cell number coordinate regardless of the intensity level of light incident on the linear scanned array. Step 80 involves searching from START to END for the greatest positive area defined by the second derivative, such as by numerical integration. The range-finding technique described above provides a second benefit apart from speed because it eliminates potential anomalies in the illumination curve which can sometimes cause humps in the second derivative with greater areas than the hump at the actual shadowline location. If these anomalies are not ignored, erroneous readings can result.

Figure 11:
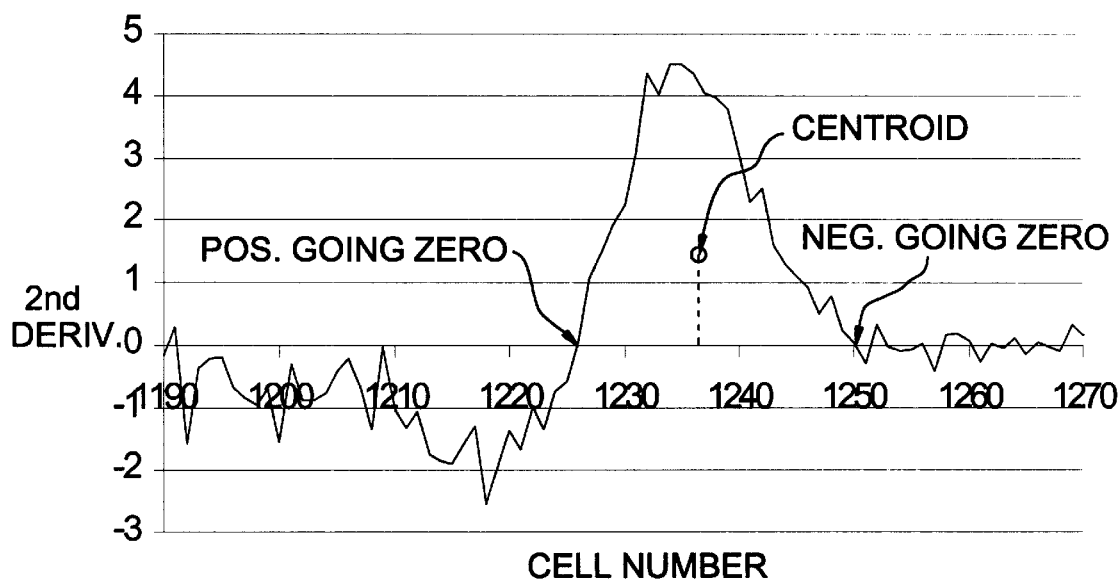
FIG. 11 is a graph showing the second derivative of a sample illumination curve in the region of the shadowline to illustrate the step of assigning a cell crossing number in accordance with the present invention.

The next step 82 is to find the "center of gravity" or centroid of the greatest positive area defined by the second derivative. Mathematically, this is done by beginning where the second derivative crosses the zero-axis going positive at the start of the greatest positive area, then integrating until the second derivative crosses zero again, going negative. This describes the total positive area of the hump. Starting again at the positive crossing, integration is again performed until the cell which brings this second integration to over one half the total area is found. The centroid is then located by stepping back one cell to go below the half-way cell, and then interpolating to find the actual cell coordinate of the centroid. As shown in FIG. 11, this cell coordinate is deemed to be the cell crossing number of the shadowline, and is stored as such in at step 84 of FIG. 6.

As discussed above, the cell crossing number of shadowline 9 changes depending upon the index of refraction of sample substance 16. Consequently, since the optical path and other physical properties of optical means 14 are known system parameters that can be stored, the cell crossing number can be used to calculate the index of refraction. The index of refraction is reported directly as output, or is converted to a more useful form such as percent solids. It is also possible to calculate and report temperature compensated readings if a temperature sensor is provided to measure the temperature of sample substance 16.

The method of the present invention provides improved precision (repeatability) of refractometer measurements even where there is a wide range of light intensities involved. Improved measurement accuracy follows improved precision because the accuracy is "calibrated in" using samples having well-known characteristics before any readings are taken. Thus, the present method for shadowline determination is applicable in both reflected light and transmitted light automatic refractometers, and is potentially suitable for other applications.

What is claimed is:

1. A method for determining a cell crossing number of a shadowline between an illuminated region and an adjacent dark region on a linear array having a plurality of photosensitive cells, said method comprising the steps of:

A) scanning said array to extract a response signal from each of said plurality of cells, the amplitude of said response signal being determined by the amount of illumination of the corresponding cell by incident light;

B) converting said response signals from said scanned array into digital signals containing information as to the amplitudes of said response signals from said array, said digital signals collectively representing an illumination distribution curve with respect to said array;

C) establishing a range of cells of said linear scanned array within which said shadowline resides;

D) calculating the second derivative of said illumination distribution curve over said range of cells;

E) identifying the greatest positive area bounded by said second derivative;

F) finding the centroid of said greatest positive area; and

G) assigning the cell number coordinate of said centroid to be said cell crossing number.

2. The method according to claim 1, further comprising the step of applying a dark current correction to said illumination distribution curve.

3. The method according to claim 1, further comprising the step of applying a moving average filter to said illumination distribution curve.

4. The method according to claim 1, wherein said step of establishing a range of cells comprises the sub steps of:

C1) finding the brightest cell receiving the greatest amount of illumination by looking for a peak cell amplitude;

C2) searching from the brightest cell in the direction toward said dark region to locate a range start cell having a corresponding amplitude that is a approximately a predetermined percentage of said peak cell amplitude; and C3) continuing to search from said range start cell in said direction to locate a range end cell meeting any one of a plurality of range end cell criteria.

5. The method according to claim 4, wherein said plurality of range end cell criteria comprises said range end cell having a corresponding amplitude that is at least a predetermined percentage increase over a dimmest cell amplitude of cells in said range.

6. The method according to claim 4, wherein said plurality of range end cell criteria comprises said range end cell being the last of said plurality of cells in said array.

7. A method for determining the index of refraction of a substance, said method comprising the steps of:

A) providing a linear scanned array having a plurality of photosensitive cells and optical means for directing light onto said array;

B) placing said substance in operative association with said optical means such that the particular photosensitive cells of said array which are illuminated by said light and a cell crossing number of a shadowline defined by illuminated and dark regions of said array are determined by the index of refraction of said substance;

C) scanning said array to extract a response signal from each of said plurality of cells, the amplitude of said response signal being determined by the amount of illumination of the corresponding cell by incident light;

D) converting said response signals from said scanned array into digital signals containing information as to the amplitudes of said response signals from said array, said digital signals collectively representing an illumination distribution curve with respect to said array;

E) establishing a range of cells of said linear scanned array within which said shadowline resides;

F) calculating the second derivative of said illumination distribution curve over said range of cells;

G) identifying the greatest positive area bounded by said second derivative;

H) finding the centroid of said greatest positive area;

I) assigning the cell number coordinate of said centroid to be said cell crossing number; and J) calculating said index of refraction based on said cell crossing number.

8. The method according to claim 7, further comprising the step of applying a dark current correction to said illumination distribution curve.

9. The method according to claim 7, further comprising the step of applying a moving average filter to said illumination distribution curve.

10. A refractometer comprising:

a linear scanned array comprising a plurality of photosensitive cells, each cell providing a response signal during a scan and the amplitude of each response signal being determined by the amount of illumination of the corresponding cell by incident light;

optical means for directing light onto said array, the particular photosensitive cells of said array which are illuminated by said light and a cell crossing number of a shadowline defined by illuminated and dark regions of said array being determined by the index of refraction of a substance placed in operative association with said optical means;

analog to digital conversion means for converting said response signals from said linear scanned array into digital signals containing information as to the amplitudes of said response signals from said array, said digital signals collectively representing an illumination distribution curve with respect to said array;

digital processing circuit means for calculating the second derivative of at least a portion of said illumination distribution curve in which said shadowline is represented, identifying the greatest positive area bounded by said second derivative, finding the centroid of said greatest positive area, assigning a cell coordinate of said centroid to be said cell crossing number, and calculating said index of refraction based on said cell crossing number; and an output device connected to said digital processing circuit means for reporting a measurement value based on said index of refraction of said substance.

* * * * *